United States Patent [19]

Johnson et al.

[11] Patent Number: 4,610,965

[45] Date of Patent: Sep. 9, 1986

[54] ADSORPTION-DESORPTION PURIFICATION OF GLUCOSE ISOMERASE

[75] Inventors: Richard A. Johnson; Richard L. Antrim, both of Clinton, Iowa; Norman E. Lloyd, Ridgefield, Conn.

[73] Assignee: Nabisco Brands, Inc., Parsippany, N.J.

[21] Appl. No.: 684,204

[22] Filed: Dec. 20, 1984

[51] Int. Cl.[4] .............................................. C12N 9/92
[52] U.S. Cl. .................................... 435/234; 435/815
[58] Field of Search ................................ 435/234, 815

[56] References Cited

U.S. PATENT DOCUMENTS 4,256,838 3/1981 Jackson et al. ..................... 435/234
4,263,400 4/1981 Ushiro ................................ 435/177

Primary Examiner—Lionel M. Shapiro
Attorney, Agent, or Firm—Richard Kornutik

[57] ABSTRACT

The present invention relates to a process for the production of a purified glucose isomerase which comprises contacting an impure extract containing glucose isomerase and soluble impurities with a weakly basic ion exchange material known to adsorb glucose isomerase; adding a first salt solution of a concentration which removes unadsorbed and weakly adsorbed impurities, but not glucose isomerase; and adding a second, buffered salt solution which elutes the adsorbed glucose isomerase.

15 Claims, No Drawings

ADSORPTION-DESORPTION PURIFICATION OF GLUCOSE ISOMERASE

FIELD OF THE INVENTION

The present invention relates to a process for enzyme purification More specifically, the invention relates to a method for purification of glucose isomerase.

BACKROUND OF THE INVENTION

The use of enzyme extracts from microorganisms in industry is widespread and quite profitable. Among the more common enzymes produced in a larger scale are bacterial proteases for use in making detergent powders, glucose oxidase for food preservation, and glucanases in the brewing industry. Many enzymes isolated for industrial use are extracellular, i.e., excreted into the growth medium by the microorganism; isolation of such enzymes is usually a relatively simple matter. However, as is the case with, for example, glucose oxidase, many enzymes are produced intracellularly; extraction of the enzyme and removal of contaminants such as cellular debris and unwanted proteins presents an additional difficulty to the larger scale use of such products.

One particularly valuable intracellularly produced enzyme is glucose isomerase. This enzyme is produced by a wide variety of microorganisms, and is used to enzymatically catalyze the conversion of glucose, a relatively unsweet but inexpensive sugar to the sweeter sugar, fructose Examples of known procedures for this conversion may be found in Hamilton, et al. ("Glucose Isomerase, a Case Study of Enzyme-Catalyzed Process Technology" Immobilized Enzymes in Food and Microbial Processes, Olson, et al., Plenum Press, New York, (1974), pp. 94–106, 112, 115–137); and a number of other publications (Antrim, et al. "Glucose Isomerase Production of High-fructose Syrups", *Applied Biochemistry and Bioengineering,* Vol. 2, Academic Press (1979); Chen, et al., Glucose Isomerase (a review)", *Process Biochem.,* (1980), pp. 36–41; Thompson, et al. "Fructose Manufacture from Glucose by Immobilized Glucose Isomerase", *Chem. Abstracts,* Vol. 82, (1975), Abs. No. 110316h; and Takasaki, "Fructose Production by Glucose Isomerase", *Chem. Abstracts,* Vol. 81, (1974), Abs. No. 7647.

Although the enzyme is water soluble, performing the reaction in an aqueous solution presents the difficulty and expense of recovering the enzyme; a single use of the enzyme may also be rather costly. There are therefore a number of techniques for isomerization which involve immobilizing the enzyme so that substantial activity is retained while the enzyme is fixed to a water insoluble matrix. This arrangement allows for the repeated use of the enzyme for prolonged periods of time and with a number of different glucose containing solutions.

For such a system to function at maximum efficiency the immobilized enzyme should preferably be as pure as possible. This allows not only maximum loading, but also provides maximum specificity during conversion by ensuring a homogeneous enzyme product. A number of types of purification methods now exist. U.S. Pat. No. 4,007,842 describes a method in which a water insoluble organic solvent is added to an aqueous solution of this enzyme, causing precipitation of non-enzyme material, followed by treating the remaining solution with a soluble magnesium salt, which then causes the precipitation of an enzyme-magnesium complex. While effective, the method described therein is time-consuming and relatively expensive. U.S. Pat. No. 4,250,263 describes a system in which a crude glucose-isomerase composition is heat-treated to precipitate non-enzyme material, leaving a glucose-isomerase containing solution. Although this method is somewhat simpler than that noted above, the relative purity of the heat-treated solution is not very high.

Immobilized glucose isomerase is frequently employed to prepare high fructose corn syrups. In the course of such a process, the use of a purified enzyme offers certain distinct advantages. For example, a higher activity level will generally be associated with an immobilized enzyme which has been at least partially purified prior to the reaction. This higher activity will in turn provide a longer effective operating time for the reactor. It is thus preferable to remove as much in the way of associated impurities as is possible prior to immobilization.

The disadvantages of most of the preceding methods of purification lie in the relative complexity of the processes involved. It would be desirable to find a procedure which would be simplified with respect to processing time, while still providing a large capacity and a resulting enzyme preparation which has a high level of purity.

The present invention satisfies all these criteria for an efficient glucose isomerase purification method. The subject process relates to purification of the desired enzyme by an adsorption-desorption technique which is rapid and relatively uncomplicated, and yet produces an enzyme of surprising purity, eminently well-suited for use in providing immobilized glucose isomerase of high activity. There are some previously known methods for adsorption-desorption purification of glucose isomerase, but these are generally more cumbersome, time-consuming or produce potentially less pure product. For example, U.S. Pat. No. 4,256,838 describes a technique in which nucleic acids are first precipitated out of an isomerase-containing solution by heat treatment, followed by addition of the resulting solution to a chromatographic column, and subsequent elution of the enzyme. The required precipitation step prior to the adsorption of the enzyme presents a complication not required in the process of the present invention. A different type of chromatographic technique is disclosed in U.S. Pat. No. 4,347,322. In the method described therein, an impure enzyme extract is added to an ionic exchange material to which both the enzyme and ionic impurities are adsorbed. As additional extract is added, enzyme begins to appear in the effluent; presumably, the enzyme is being displaced by more strongly adsorbed impurities. Eventually, as more of the impure preparation is added, a relatively pure enzyme is collected in the effluent. This process also differs from the present invention in that it accounts for the removal of only the strongly adsorbed impurities.

BRIEF DESCRIPTION OF THE INVENTION

The present invention relates to a process for the production of a purified glucose isomerase which comprises contacting an impure extract containing glucose isomerase and soluble impurities with a weakly basic ion exchange material known to adsorb glucose isomerase; adding a first salt solution of a concentration which removes unadsorbed and weakly adsorbed impurities, but not glucose isomerase; and adding a second, buffered salt solution which elutes the adsorbed glucose isomerase.

DETAILED DESCRIPTION OF THE INVENTION

The present invention provides a simple, efficient method for the purification of glucose isomerase which requires a minimum of steps and inexpensive materials, while still producing a highly purified enzyme product. Furthermore, it is particularly effective in that it not only eliminates strongly adsorbed impurities, it also eliminates unadsorbed and weakly adsorbed impurities. The basic procedure involves adding an isomerase extract to a suitable carrier, washing the column with a salt solution of a concentration which is not sufficient to elute the glucose isomerase, but which will wash off any unabsorbed or weakly adsorbed impurities, and then washing the column with a buffered salt solution of a concentration which will specifically elute the glucose isomerase, but not the strongly adsorbed impurities.

The procedure may be performed with an enzyme extract derived from virtually any source. Methods to produce the glucose isomerase extracts used as starting materials in the process of the present invention are well known in the art. For example, an enzyme extract containing glucose isomerase may be obtained by fermentation of microorganisms of a species known to produce glucose isomerase, extracting the enzymes from the mycelia and removing insoluble material by known methods.

The preferred glucose isomerase extracts may be obtained from microorganisms of the genera Actinoplanes, Ampullariella, Aerobacter, Arthrobacter, Bacillus, Micromonospora, Microbispora, Microellobospora, Norcardia, or Streptomyces. Glucose isomerase extract typically may be obtained from microorganisms of the species *Streptomyces rubigenosus, Streptomyces olivochromogenes, Bacillus coagulans* or *Bacillus stearothermophilus.*

It is preferred that the enzyme extract be clarified to some extent prior to addition to the column, in order to assure efficient processing on the column. This can be most easily accomplished by filtration, which will remove any suspended solids that might affect column performance. The prior filtrate should be clear, and the pH should be adjusted to between about 5–10; and preferably about 6–8, with 6.8–7.2 being the most preferred range. Continuous monitoring and readjustment should be performed if necessary during application.

The material used for the column may be any weakly basic ion exchange resin, such as DEAE cellulose, Amberlite IRA-93, Diaion UA-30, Diaion WA-11, Amberlite IR-45 or Duolite ES-561, 562 or 568. Most particularly preferred as the enzyme carrier for the present process is granular DEAE cellulose (GDC), as described in Antrim etal., U.S. Pat. No. 4,355,117.

After loading of the enzyme onto the column, an initial washing is performed to remove those impurities in the extract which are only weakly adsorbed to the column, or not adsorbed at all. For this purpose, the column is washed with a dilute solution of an electrolyte.

A wide range of solutions may be useful in this regard. The major criterion for selection of the electrolyte is that it not be harmful to the enzyme: for example, Ca or Hg salts may be unsuitable for this procedure. As employed herein, in the specification and the claim the term "electrolytic solution" means a solution containing a strong electrolyte which tends to 100% dissociation at the concentrations employed. Salts are generally most preferred. Among the salts meeting the aforementioned criteria are NaCl, KCl, $Na_2SO_4$, $K_2SO_4$, $NaNO_3$, $KNO_3$, $Mg^{+2}$, $Mn^{+2}$ and $Co^{+2}$ salts, $NH_4Cl$, $(NH_4)_2SO_4$ and pyridinium chloride, with NaCl being preferred. Also useful are sodium, potassium, and ammonium acetate, citrate and maleate salts, provided they are used within a pH range consistent with their function as electrolytes. Ionic polymers may be used, but are not particularly practical. Specifically not recommended for use are heavy metal and transition metal (e.g. $Ag^+$, $Al^{+3}$, $Fe^{+2}$) salts. Under carefully controlled conditions acids and bases may also be utilized. However, the high dilution required, the possibility of enzyme denaturation, and the lower yields obtained with the use of acids and bases make salt solutions preferable. The potential utility of additional types of salts may be readily determined by performing a series of trial elutions, which involves preparing small granular DEAE cellulose columns, loading enzyme onto the column, washing the column with the salt of interest, and monitoring the eluate for enzyme activity. Variation in the preferred concentration required for the different salts or for use with extracts of different microorganisms may also be determined by similar methods.

The preferred salt concentration for the dilute wash is between about 0.05 to about 0.2N NaCl, with a concentration of about 0.1–0.18N being particularly preferred. The effluent can be monitored for conductivity of the particular salt solution. Subsequent to removal of weakly bound impurities, the isomerase is then eluted with a second buffered salt solution of at least about 0.3NaCl. It is preferred however, that the concentration be about 0.45N up to below 1N. The more concentrated solution will elute the glucose isomerase, but leave the strongly adsorbed impurities bound to the column. Generally speaking, about 95% of the enzyme activity applied to the column will be eluted with a total of 1.5–2.0 bed volumes of effluent. The pH of the enzyme solution should be monitored and adjusted preferably to between 6–8, and most preferably to between 6.8–7.2 prior to further processing. Any traditional buffer may be utilized for this pupose. The potency of the eluted enzyme will generally be at least 80, and up to 150 IGIU/ml.

As an optional step, the eluted enzyme may be desalted and concentrated by ultrafiltration after an initial filtration to remove any insoluble material. Excellent results are obtained using membranes with molecular weight cutoffs of 30,000 or 50,000; the enzyme can be concentrated 20–40 fold in this manner with little loss of activity or membrane flux rate. The concentrated enzyme may then be diafiltered with water and a buffered solution to improve storage stability. Overall recovery of activity across the ultrafiltration step will usually be at least 95% of the starting extract activity.

One of the advantages of this system is that the column may be easily regenerated following enzyme elution. After elution, the column may be washed with a very concentrated salt solution (at least 1N NaCl) which will remove the strongly adsorbed materials which were not removed by the weaker salt solutions. This is immediately followed by water wash to remove the salt, and a wash with a buffer solution to restore pH to 6–8. At this point the column is ready for another cycle of operation. The column should be stripped with 0.1N NaOH periodically, about once every 5 to 10 cycles, in order to remove materials which have not been removed by the salt regeneration. This also provides a sanitizing effect by inactivation and removal of microbial contaminants.

The process also has the advantage of being fairly rapid; a complete cycle of operation can be accomplished in less than 10 hours, so that at least two cycles can be completed in a day. Monitoring of column performance is also fairly simple, particularly when using measurements based on color, conductivity and U.V. A continuous U.V. monitor is particularly useful in detecting the breakthough in enzyme elution, since this is indicated by at least a 10-fold increase in $A_{280}$, due to the absorbance by aromatic residues of the protein.

The process of the present invention may be better understood by reference to the following example, which should not be construed as limiting the scope of the invention.

EXAMPLE 1

The following example illustrates the complete cycle of the process from extract filtration through purification to final filtration.

A clarified extract of glucose isomerase suitable for processing on a column of granular DEAE-cellulose was prepared. Such an extract containing about 30 IGIU/ml can be produced from Streptomyces sp. ATCC 21175 according to the teachings of Example I in U.S. Pat. No. 3,788,945.

The column was prepared by suspending 300 g d.b. GDC, in about 2000 ml of 10 mM Tris buffer, pH 7. The resulting slurry was deaerated for two hours under laboratory vacuum and then poured into a 5×80 cm Glenco chromatography column and allowed to settle by gravity. The resulting bed dimensions were 5×64 cm for a total bed volume of 1250 ml.

For a typical isomerase extract containing about 30 IGIU/ml (for a definition of IGIU enzyme units and the method of assay, see "Automated Method for the Determination of D-Glucose Isomerase," N.E. Lloyd et al., *Cereal Chemistry* 49(50: 544–553, 1972), , the 300 g bed of GDC had an estimated capacity of over $3 \times 10^5$ IGIU based on preliminary column experiments. To leave sufficient margin for error and provide extra adsorptive capacity the ideal batch size for a single cycle would be about $2.4 \times 10^5$ IGIU (800 IGIU/g GDC 75% of capacity). The isomerase extract, after adjusting the pH to 6.8–7.1 was pumped directly into the column at a flow rate of 3 bed volumes (B.V.) per hour (20 ml/min). This slower flow rate allowed ample residence time for adsorption-equilibration. During the enzyme loading step the column effluent was checked for isomerase activity and UV absorbance.

After all of the enzyme had been pumped into the column bed, the column was washed with dilute salt solution (0.15 N NaCl) at a flow rate of 4 B.V. per hour (80 ml/min) for a total of about one hour. This step removed unadsorbed and weakly adsorbed impurities. The effluent was monitored for isomerase activity, U.V. absorbance, and visible color. In the final stages of washing, the effluent contains very little visible color or U.V. absorbance. The effluent was also monitored for conductivity to establish a baseline for the 0.15 N salt solution After a total of 4 B.V. of wash solution had been applied, the enzyme was eluted with buffered salt solution (0.45 N NaCl, 1 mM MgSO$_4$, 10 mM Tris, pH 7.0) at a flow rate of 1.5 B.V. per hour (20 ml/min). Enzyme desorption occured as the salt front moved down the column, and enzyme began to appear in the effluent when one void volume (70% of B.V.) of salt solution had been applied to the column. Elution of the enzyme was accompanied by a sharp increase in conductivity, color, and U.V. absorbance. When the enzyme began to elute the effluent was collected until a total of 1.5–2.0 B.V. had accumulated and the U.V. absorbance had indicated that enzyme elution was nearly complete. At this point at least 95% of the activity applied to the column was eluted. The pH of the eluted enzyme solution was checked and adjusted to 6.8–7.0 when necessary before further processing. The potency of the eluted enzyme solution generally ranged from 80–150 IGIU/ml depending on the volume of the eluate collected.

After enzyme elution the column was regenerated by washing with 2 B.V. of 1 N NaCl solution at a flow rate of 5 B.V. per hour. This step removes strongly adsorbed materials not desorbed by the weaker salt solutions. The salt wash was followed immediately by a water wash at a flow rate of 5 B.V. per hour for about one hour to remove residual salt. The water wash was then followed by a wash with 50 mM Tris pH 7.0 at a flow rate of 2 B.V. per hour until the effluent pH was between 6.9 and 7.1. The column was then ready for loading of enzyme and another cycle of operation.

The enzyme eluted from GDC can be desalted and concentrated by ultrafiltration after a polish filtration to remove any insoluble materials. Laboratory ultrafiltrations were carried out with an Amicon CH4 hollow fiber concentrator or with Amicon 401 and 201 stirred cells using membranes with molecular weight cutoffs (MWCO) of 30,000 or 50,000. The enzyme eluate can be easily concentrated 20–40 fold with little loss of activity or membrane flux rate. The concentrated enzyme was diafiltered twice with water ( 5 vols. each) and once with 10 mM Tris, 1 mM Mg$^{++}$, pH 7.0 to remove residual salt and add buffer and metals for storage stability. The final potency ranges from 2000 to 4000 IGIU/ml depending on the extent of ultrafiltration and final retentate volume. Overall recovery of activity across the ultrafiltration step was usually about 95% of the activity eluted from the GDC column and about 85 to 90% of the starting extract activity.

What is claimed is:

1. A process for the production of a purified glucose isomerase which comprises:
  (a) contacting an impure extract which has not been previously treated to remove soluble impurities, said extract containing glucose isomerase ans soluble impurities with a weakly basic ion exchange material known to adsorb glucose isomerase,
  (b) adding a first salt solution of a concentration of about 0.05-0.2N which removes unadsorbed and weakly adsorbed impurities, but not glucose isomerase.
  (c) adding a second, buffered salt solution of a concentration of at least 0.3N which elutes the adsorbed glucose isomerase.

2. The process of claim 1 wherein the salt is NaCl, KCl, K$_2$SO$_4$, NaSO$_4$, NaNo$_3$, KNO$_3$, NH$_4$Cl, (NH$_4$)$_2$SO$_4$, pyridinium chloride magnesium salts manganese salts, cobalt salts, sodium acetate, sodium maleate, sodium citrate, potassium acetate, potassium maleate, potassium acetate, ammonium acetate, ammonium maleate, or ammonium citrate.

3. The process of claim 2 wherein the salt is NaCl.

4. The process of claim 3 wherein the first salt solution is about 0.15N NaCl.

5. The process of claim 3 wherein the second salt solution is about 0.45N NaCl.

6. The process of claim 1 wherein the pH of the salt solutions is about 5–10.

7. The process of claim 6 wherein the pH is 6–8.

8. The process of claim 7 wherein the pH is 6.8–7.2.

9. The process of claim 1 wherein the ion exchange material is DEAE-cellulose.

10. The process of claim 1 which comprises the further step of concentrating the enzyme.

11. The process of claim 10 wherein the enzyme is concentrated by ultrafiltration.

12. The process of claim 10 which comprises the further step of desalting the enzyme.

13. The process of claim 12 wherein the enzyme is desalted by diafiltration.

14. The process of claim 11 wherein ultrafiltration is performed on a membrane with a molecular weight cutoff of about 30,000–50,000.

15. The process of claim 13 wherein filtration is performed on a membrane with a molecular weight cutoff of about 30,000–50,000.

* * * * *